United States Patent [19]

Stein et al.

[11] Patent Number: 4,617,157

[45] Date of Patent: Oct. 14, 1986

[54] FRAGRANCE DISPENSER FOR ROOM AIR CONDITIONER

[75] Inventors: Ray J. Stein, Pigeon Township, County of Vanderburgh; Raymond G. Simons, Knight Township, County of Vanderburgh, both of Ind.

[73] Assignee: Whirlpool Corporation, Benton Harbor, Mich.

[21] Appl. No.: 725,805

[22] Filed: Apr. 22, 1985

[51] Int. Cl.$^4$ ............................................. A61L 9/12
[52] U.S. Cl. .................................... 261/96; 239/57; 239/58; 422/124; 261/DIG. 65
[58] Field of Search ................... 422/123, 124, 5; 239/56, 57, 58, 59, 60; 261/DIG. 65, 96, 52

[56] References Cited

U.S. PATENT DOCUMENTS

| 1,080,716 | 12/1913 | Rand, Jr. ............... 239/55 |
| 1,131,307 | 3/1915 | Wunschow . |
| 1,528,640 | 3/1925 | Tvrzicky et al. . |
| 1,954,893 | 5/1933 | Saeks . |
| 2,352,075 | 6/1944 | Brownstein ............... 239/58 |
| 2,369,375 | 2/1945 | Sonntag . |
| 2,438,129 | 3/1948 | Rich ............... 239/59 |
| 2,556,608 | 6/1951 | Will ............... 239/58 |
| 2,681,827 | 6/1950 | Racz . |
| 2,734,769 | 2/1956 | Holz ............... 239/57 |
| 2,759,228 | 8/1956 | Gordon . |
| 2,778,678 | 1/1957 | Shields et al. ............... 422/124 |
| 3,021,692 | 3/1961 | Gaugler . |
| 3,434,300 | 3/1969 | Rueth et al. . |
| 3,521,816 | 7/1970 | Wilson ............... 239/60 |
| 3,527,405 | 9/1970 | Harding ............... 239/58 |
| 3,902,877 | 9/1975 | Swaim . |
| 3,923,934 | 12/1975 | Watkins ............... 239/59 |
| 3,930,797 | 1/1976 | Gertz ............... 422/124 |
| 3,990,848 | 11/1976 | Corris ............... 422/124 |
| 4,155,500 | 5/1979 | Dutcher ............... 239/59 |
| 4,279,373 | 7/1981 | Montealegre ............... 239/59 |
| 4,306,892 | 12/1981 | Atalla et al. . |
| 4,523,870 | 6/1985 | Spector ............... 239/59 |
| 4,549,693 | 10/1985 | Barlics ............... 239/55 |

FOREIGN PATENT DOCUMENTS

| 2344880 | 3/1975 | Fed. Rep. of Germany ........ 239/58 |
| 464850 | 4/1937 | United Kingdom ............... 239/56 |

*Primary Examiner*—Tim Miles
*Attorney, Agent, or Firm*—Hill, Van Santen, Steadman & Simpson

[57] ABSTRACT

An adjustable fragrance dispenser for an appliance has a mounting base, a fragrance cartridge selectively attachable to the base and a reciprocal slide having a pair of spaced shutters for selectively closing dispensing openings on corresponding walls of the cartridge. One of the shutters is spaced further from the base than the other to provide for removal and replacement of the cartridge.

13 Claims, 8 Drawing Figures

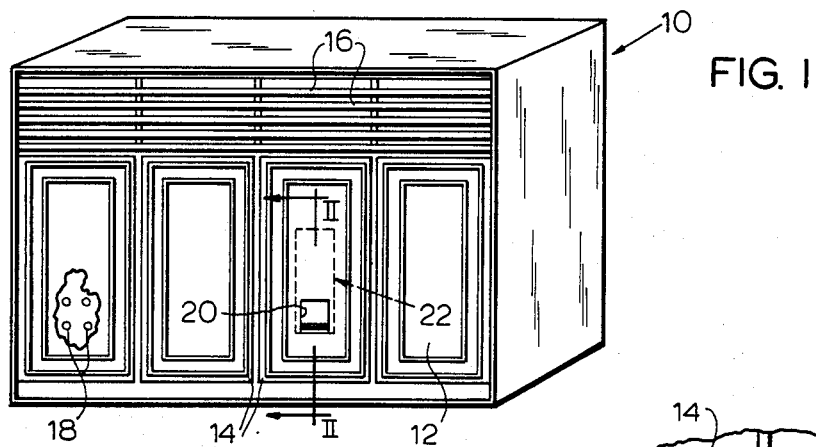
FIG. 1
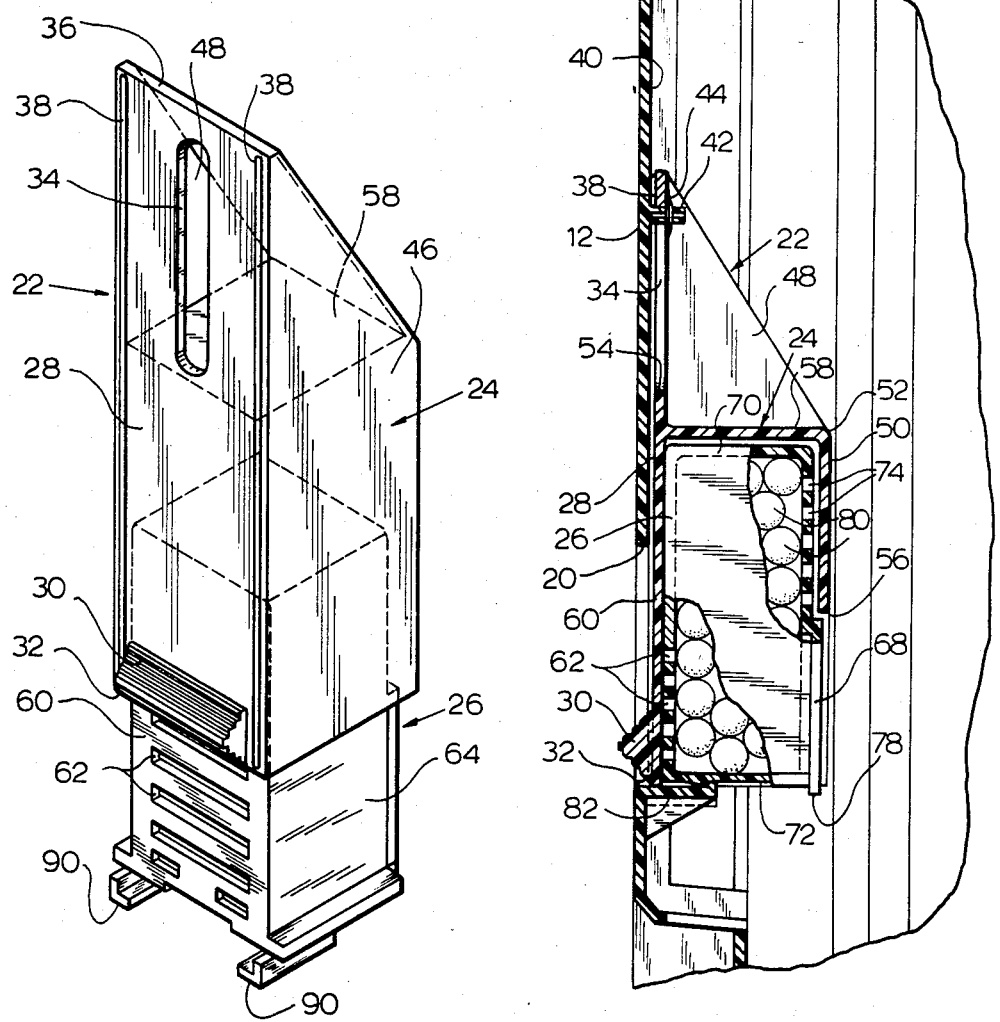
FIG. 3
FIG. 2

FIG. 4
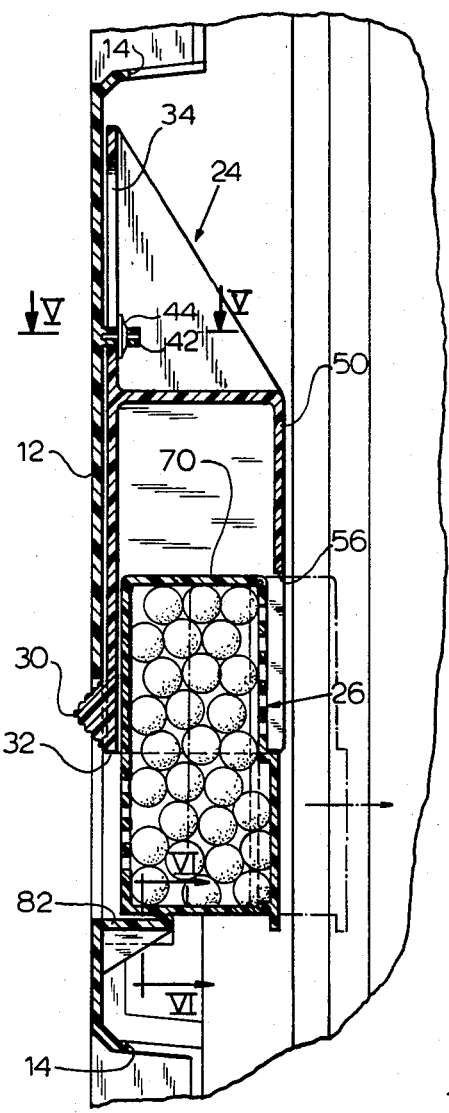
FIG. 5
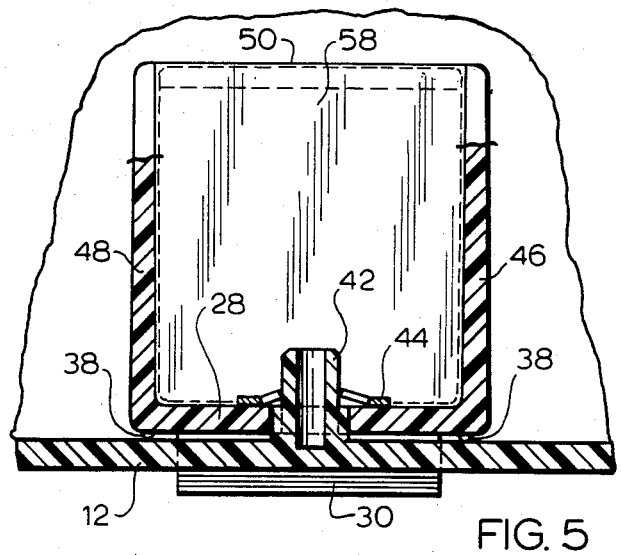
FIG. 6
FIG. 7
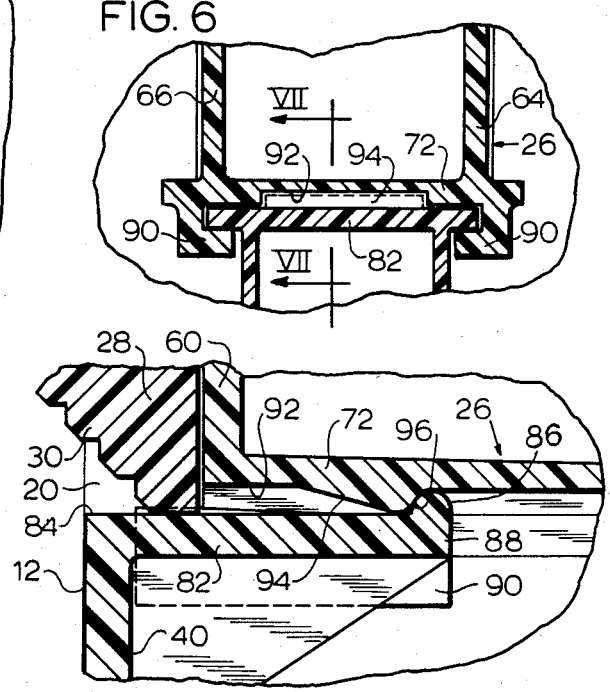
FIG. 8
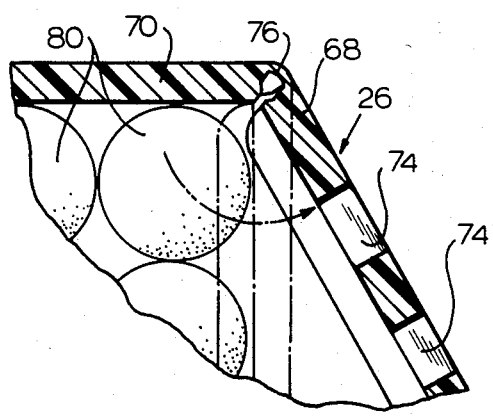

FRAGRANCE DISPENSER FOR ROOM AIR CONDITIONER

BACKGROUND OF THE INVENTION

1. Field of the Invention

This invention relates to a fragrance dispenser and more particularly to a dispenser for use with an air conditioner or other domestic appliance with a refillable or disposable fragrance pellet cartridge and having selectively movable vent shutters.

2. Description of the Prior Art

Various types of fragrance dispensers are known in the art. U.S. Pat. No. 1,131,307 discloses a fragrance dispensing device that is mountable on a fan and has parallel perforated walls through which the air stream will flow, dispensing the fragrance. The holes in each of the perforated walls can be selectively opened or closed by rotating a member having openings alignable therewith. In U.S. Pat. No. 2,369,375 an air freshening device is regulated by movement of a slide valve 34 shown in FIG. 11. U.S. Pat. No. 2,681,827 discloses a fragrance dispenser having a removable, refillable cup 13 containing dispensing holes which adjustably interact with holes in a base member to provide adjustment in the rate of dispensing.

SUMMARY OF THE INVENTION

The present invention provides a user-adjustable fragrance dispenser for an appliance useable with a fragrance pellet container or cartridge that can be either refillable or disposable. The fragrance dispenser is to be used in association with a household appliance which generates an air stream or which is the locus of unpleasant odors. For example, a room air conditioner has a room air circulating fan for taking room air into the appliance and passing it back into the room as conditioned air. Included in the term air conditioner is a device which dehumidifies but does not cool the air. The fragrance dispenser of the present invention can be mounted on such a room air conditioner to operate in cooperation with the normal air conditioning function to dispense a pleasing fragrance in the circulating air to mask odors therein. A feature of the present invention is that it is adjustable by the user to control the amount of air passing through the fragrance dispenser.

Another example of an appliance with which the present invention can be used is a trash compactor which is used to compress the volume of refuse generated in a household. Such an appliance is sometimes the source of unpleasant odors and the opening and closing of the access door to the compactor container would provide sufficient air flow to operate the dispenser.

The fragrance dispenser has two components: a dispenser body that is physically attached to the appliance and a fragrance cartridge or container which is useable with the dispenser body. The cartridge is rectilinear in shape and may be formed either as a removable prefilled unit, and thus disposable, or it may be openable and refillable with separate fragrance pellets. A refillable cartridge may be removable from or permanently affixed to the appliance. The dispenser body is slidingly attached to the appliance in the location of an air stream. A front and back wall of the dispenser body act as shutters to selectively cover or expose vent holes in the cartridge as desired by the user. The shutters move simultaneously and are operable from the exterior of the appliance. When the dispenser body is moved into the upwardmost position, the rear shutter clears the top of the cartridge to allow the cartridge to be either replaced or replenished with new fragrance pellets.

BRIEF DESCRIPTION OF THE DRAWINGS

FIG. 1 is a perspective view of a room air conditioner including a fragrance dispenser embodying the principles of the present invention.

FIG. 2 is a side sectional view of the fragrance dispenser in the closed position.

FIG. 3 is a perspective view of the fragrance dispenser.

FIG. 4 is a side sectional view of an alternate embodiment of the fragrance dispenser in the open position.

FIG. 5 is a sectional view taken generally along the line V—V of FIG. 4.

FIG. 6 is a partial sectional view taken generally along the line VI—VI of FIG. 4.

FIG. 7 is a partial sectional view taken generally along the line VII—VII of FIG. 6.

FIG. 8 is a partial sectional view of the hinge area of the cartridge containing the fragrance pellets.

DESCRIPTION OF THE PREFERRED EMBODIMENTS

Although the fragrance dispenser of the present invention can be utilized in a wide range of domestic appliances as well as in other areas in which there is some local air flow, the description of the present invention will be explained in terms of its use as an accessory to a room air conditioner as a specific example. It should be understood that we do not wish to limit the scope of the invention for use only with a room air conditioner, but rather we are explaining the invention by use of the air conditioner as a specific example.

In FIG. 1 there is shown a domestic appliance generally at 10 which comprises a room air conditioner. The air conditioner has a front air intake panel 12 having a plurality of air intake openings 14 therethrough and a plurality of air outlet openings 16 to permit recirculation of air within the room. Located behind the air intake panel 12 are a number of controls 18 for selecting and adjusting the desired temperature and air flow rate.

A rectangular opening 20 is provided in the front panel 12 behind which is mounted an air fragrance dispenser 22 shown in greater detail in FIGS. 2-8.

FIGS. 2 and 3 show the fragrance dispenser 22 which is comprised of a dispenser slide 24 and a fragrance cartridge or container 26. The dispenser slide 24 has an elongated rectangular front wall 28 which has a manual grip bar 30 near a bottom end 32 thereof and an elongated vertical slot 34 near a top end 36 thereof. Extending vertically along the lateral sides of the wall 28 are a pair of projecting runners 38, 38 which engage a rear surface 40 of the front panel 12 of the air conditioning unit 10. The grip bar 30 projects through the rectangular opening 20 in the panel 12.

A rearwardly projecting stud 42 (FIGS. 2 and 5) is captured in the slot 34 and a retaining nut 44 holds the dispenser slide 24 on the stud 42. With the dispenser slide so held against the front panel 12 of the air conditioner, the only movement available to the dispenser slide is a vertical reciprocal sliding movement limited by the length of the slot 34. The runners 38, 38 provide a low friction surface between the dispenser slide 24 and the front panel 12. The grip bar 30 can be manually operated from the front of the air conditioner 10 to move the dispenser slide up and down on the stud 42. FIG. 2 shows the full downward or closed position of the dispenser slide 24 and FIG. 4 shows the full upward or open position.

The dispenser slide 24 has a pair of parallel side walls 46, 48 which are joined at a rear side by a rear wall 50. A top end 52 of the rear wall 50 is positioned below a bottom end 54 of the slot 34 and a bottom end 56 of the rear wall 50 is positioned above the bottom end 32 of the front wall 28. Thus, the rear wall extends vertically opposite a central portion of the front wall. A solid top wall 58 connects the top end 52 of the rear wall 50 with the front wall 28. The dispenser slide 24 has an open bottom and a partially opened back below the bottom end 56 of the rear wall 50.

The fragrance cartridge 26 is rectilinear in shape and is sized to fit closely within the cavity formed by the front, rear and side walls of the fragrance dispenser slide 24. The cartridge 26 has a front wall 60 with a plurality of horizontal dispensing slots or vents 62 through the bottom half of the wall 60. The cartridge 26 has a pair of parallel opposed side walls 64, 66, a rear wall 68, a top wall 70 and a bottom wall 72. A plurality of horizontal dispensing slots or vents 74 are provided in the upper half of the rear wall 68. The remainder of all the walls are solid.

As best seen in FIG. 8, the rear wall 68 may be attached to the top wall 70 by means of a living hinge 76 which permits the rear wall 68 to be opened thus exposing the interior of the cartridge 26. A bottom end 78 of the rear wall 68 extends below the bottom wall 72 to provide a griping flange to assist in the opening of the rear wall 68. In this manner, the container 26 can be selectively opened by a user to charge the interior of the container with a plurality of fragrance pellets 80 or to replenish the supply of such pellets as they lose their fragrance. Alternatively, the rear wall 68 could be permanently secured to the side walls 64, 66 and bottom wall 72 as illustrated in FIG. 4, without a living hinge, in which case the cartridge 26 would be disposable rather than refillable.

The air intake panel 12 of the air conditioner 10 has a rearwardly projecting finger 82, best shown in FIG. 7, at a bottom end 84 of the rectangular opening 20 which forms a mounting base for the cartridge 26. The finger 82 has a ridge 86 extending laterally along a central portion of a rear edge 88. The cartridge 26 may have a pair of laterally spaced rails 90, 90 formed below the bottom wall 72 to slidingly engage side edges of the finger 82 as best shown in FIG. 6. A central portion 92 of the cartridge bottom wall 72 is recessed to permit the ridge 86 to pass unrestricted below the bottom wall 72. A ramp 94 (FIG. 7) is positioned in the recessed area 92 which causes the ridge 86 to cam away from the bottom wall 72 as the cartridge 26 is being slipped onto the mounting base finger 82. A back edge 96 of the ramp 94 is angled only slightly from vertical to act as a detent to capture and retain the ridge, thereby locking the cartridge 26 on the finger 82. The cartridge 26 is thus made removable from the finger 82. However, a force greater than normal vibration of the machine is required for such removal.

The rails 90 extend forwardly beyond the front wall 60 of the cartridge 26 to engage the rear face 40 of the front panel 12 to hold the cartridge 26 in a fixed preselected position on the finger 82 to prevent the cartridge front wall 60 from binding with the dispenser slide front wall 28 during vertical movement of the dispenser slide front wall 28, but at the same time assuring that the two walls 28, 60 are closely adjacent. Thus the cartridge 26 is locked in a position defined by the engagement of the rails 90 with the rear face 40 of the front panel 12 and the ridge 86 locked on the rear edge 96 of the ramp 94. This positive lock prevents vibration of the cartridge during operation of the appliance.

Alternatively, cartridge 26 may be fixedly attached to rearwardly projecting finger 82, without rails 90, 90, ridge 86 or ramp 94, in which case cartridge 26 would be refillable in place rather than removable.

The lower half of the front wall 28 of the dispenser slide acts as a shutter to selectively cover or expose the horizontal slots 62 in the front wall 60 of the cartridge 26. Likewise, the rear wall 50 of the dispenser slide acts as a shutter to selectively cover or expose the horizontal slots 74 in the rear wall 68 of the cartridge. Thus, with the cartridge in place within the dispenser slide and the front panel 12 in place on the appliance 10, a user may, by adjusting the position of grip bar 30, selectively expose one or more of the openings in the front and rear walls of the cartridge simultaneously, thus establishing an air flow path through the interior of the cartridge 26 such that some of the air being drawn into the appliance will pass through the cartridge 26 evaporating the fragrance from the pellets 80 and carrying the fragrance with the air flow.

Enhanced air flow through the interior of the cartridge is achieved since the openings through the front and rear walls are at opposite vertical ends of the cartridge. This arrangement has the advantage of allowing the designer to vary the height of the cartridge and thus lengthen or shorten the spacing between the openings 62, 74 in the front and back of the cartridge 26. With this additional design parameter, a larger or smaller charge of fragrance pellets 80 can be provided in the cartridge 26, with respect to the cross-sectional area thereof, assuring that a maximum full season's charge of fragrance pellets can be put into the cartridge.

To insert a removable cartridge 26 onto the base mounting finger 82, the dispenser slide 24 must first be slid upwardly on the stud 42 by pushing the grip bar 30 upwardly. When the dispenser slide 24 is in the uppermost position, the top wall 70 of the cartridge 26 will clear the bottom edge 56 of the dispenser slide rear wall 50 thus permitting the cartridge to be slid onto the finger 82. The front shutter wall 28, because it extends lower than both the rear shutter wall 50 and the top wall 70 of the cartridge 26, serves as a positioning stop to assure that when the user inserts the cartridge 26 onto the base finger 82, it will be properly located on the base finger between the two shutter walls 28, 50. Also, by extending lower than the cartridge top wall 70, even when the dispenser slide is in the fully open position, the front shutter wall 28 prevents the user or others from viewing any unsightly gaps at the top of the cartridge. When the dispenser slide 24 is moved downwardly, the cartridge 26 will be further securely held in place by the walls of the dispenser slide.

To remove the cartridge 26 for replacement or refilling, air intake panel 12 is separated from the appliance and the grip bar 30 is pushed upwardly within the opening 20 until the bottom end 56 of the rear wall 50 clears the top wall 70 of the cartridge. Then, a manual force can be applied to the cartridge in a rearward direction to dislodge the ridge 86 from the rear edge of the ramp 94 permitting rearward removal of the cartridge as shown in phantom in FIG. 4. If the cartridge is of the refillable type, the flange on the bottom edge 78 of the rear wall 68 can be pulled to open the rear wall through a pivoting action of the living hinge 76. The cartridge can then be recharged with a fresh supply of fragrance pellets 80. Alternatively, a refillable cartridge can be recharged with a fresh supply of fragrance pellets 80 without the necessity of removing the cartridge from panel 12. With the grip bar 50 pushed upwardly until the bottom end 56 of the rear wall 50 clears the cartridge top wall 70, rear wall 68 of the cartridge can be pulled open through the pivoting action of living hinge 76 even with the cartridge in place.

Although the fragrance dispenser 22 has been shown as an accessory to an air conditioner, it can also be used in other locations in which there is at least some local air flow. For example, the dispenser can be used with a trash compactor which has an openable door, the opening of the door causing a local air flow. Also, the dispenser could be mounted on a dehumidifier which has a fan for circulating room air through the appliance.

It also should be appreciated that even though the dispenser has been shown to be positioned in the air inlet portion of an air conditioner, it also could be positioned in the air outlet position thereby permitting fragrance to be added to fresh air as well as recirculated air.

Thus, the present invention provides an adjustable fragrance dispenser for an appliance having a mounting base, a fragrance cartridge attached to the base, and a reciprocal slide having a pair of spaced shutters for selectively closing openings on corresponding walls of the cartridge, wherein, one of the shutters is spaced further from the base than the other to provide means for replacement of the cartridge or the fragrance pellets within the cartridge.

As is apparent from the foregoing specification, the invention is susceptible of being embodied with various alterations and modifications which may differ particularly from those that have been described in the preceeding specification and description. It should be understood that we wish to embody within the scope of the patent warranted hereon all such modifications as reasonably and properly come within the scope of our contribution to the art.

We claim as our invention:

1. In an appliance having a panel positioned in an air flow path, a fragrance dispenser comprising:
   a cartridge mounting base secured to said panel;
   a fragrance cartridge attachable to said base at a bottom end and having a front wall and a spaced rear wall connected by side walls forming an interior chargeable with fragrance pellets;
   said cartridge having a plurality of dispensing holes through said front wall near said bottom end and a plurality of dispensing holes through said rear wall spaced away from said bottom end;
   a reciprocal slide mounted on said panel to slide along an axis between an open position distant from said mounting base and a closed position closer to said mounting base;
   said slide having a front wall and a spaced rear wall connected by side walls forming a cavity for receiving said cartridge,
   said slide front wall selectively covering said openings in said cartridge front wall and said slide rear wall simultaneously selectively covering said openings in said cartridge rear wall as said slide is axially moved;
   said slide rear wall being sufficiently short to provide clearance from said base when said slide is in said open position that exceeds the axial length of said fragrance cartridge so that the fragrance cartridge can be replaced or refilled.

2. A device according to claim 1 wherein one of said cartridge walls is selectively openable providing access to said interior of said cartridge for charging said interior with a supply of said fragrance pellets.

3. A device according to claim 1 wherein said cartridge walls are all permanently joined preventing access to the interior of said cartridge.

4. A device according to claim 1 wherein said cartridge is removably attached to said base.

5. A device according to claim 1 wherein said cartridge is fixedly attached to said base.

6. A device according to claim 1 wherein said panel has an opening therethrough adjacent to said mounting base permitting exposure of said openings in said cartridge front wall through said panel.

7. A device according to claim 6 wherein said slide front wall extends between said cartridge front wall and said panel opening to simultaneously control the effective size of said opening and the number of said dispensing holes exposed in said cartridge.

8. In an appliance having a panel positioned in an air flow path and a mounting base secured to said panel with a fragrance dispensing cartridge attached to said base, a dispenser slide comprising:
   a front wall mounted on said panel to slide along an axis between an open position distant from said mounting base and a closed position closer to said mounting base;
   a rear wall spaced from said front wall and connected to said front wall by side walls; said front wall axially longer and extending closer to said mounting base than said rear wall;
   whereby clearance is provided between said rear wall and said mounting base when said slide is in said open position to permit access to said cartridge.

9. For use with a fragrance dispenser having a mounting base, a fragrance cartridge comprising:
   a front wall having a plurality of holes therethrough adjacent to a first end;
   a base wall connected to said front wall at said first end;
   a rear wall parallel to and spaced from said front wall by said base wall and having a plurality of holes therethrough adjacent a second end opposite said first end;
   side walls connecting said front and rear walls;
   a pair of spaced track means attached to said side walls adjacent said base wall for slidably engaging said mounting base; and
   a top wall connecting said front and rear walls at said second end;
   said walls defining an interior cavity for receiving a charge of fragrance pellets;
   whereby air enters said cavity near one end of said cartridge and exits said cavity near an opposite end of said cartridge.

10. A device according to claim 9 wherein one of said walls is selectively removable to permit replacing of said fragrance pellets.

11. A cartridge according to claim 9 wherein said base wall includes a detent means engagable with said mounting base to selectively hold said cartridge on said base.

12. In an appliance having a panel defining a front side and a rear side and means creating a difference in air pressure between said front and rear panel sides, an adjustable fragrance dispenser for use with a removable fragrance cartridge having a pair of substantially flat spaced parallel walls and a predetermined length along an axis parallel with said walls, the distance between said walls defining the width of said cartridge, said walls having means defining dispensing holes therein, said dispenser comprising:

means defining a dispensing opening in said panel;
a mounting base attached to said panel rear side adjacent said opening, said mounting base defining means for rigidly retaining said cartridge;
a slide selectively reciprocable between a fully closed position adjacent said base and a fully open position spaced from said base;
a front shutter defined by said slide and facially contacting said panel rear side, said front shutter substantially covering said dispensing opening when said slide is in said fully closed position and having means defining a lower edge spaced a first distance from said base when said slide is in said fully open position, said first distance is less than said length of said cartridge;
a rear shutter defined by said slide and substantially parallel with said first shutter, the inner distance between said shutters substantially equal to said width of said cartridge, said rear shutter having means defining a lower edge spaced a second distance from said base when said slide is in said fully open position, said second distance is greater than said length of said cartridge;
and handle means to allow the slide to be selectively reciprocated;
whereby, with the slide in the fully open position a fragrance cartridge can be inserted under the rear shutter lower edge and positioned on the base in facial contact with the front shutter which will assure that the cartridge is properly aligned within the dispenser for the shutters to selectively cover the cartridge dispensing holes as the slide is selectively reciprocated.

13. In an air conditioner having a fan for circulating conditioned air and a panel positioned in the flow created by said fan, said panel defining a front side and a rear side, an adjustable fragrance dispenser mounted to said panel comprising:

means defining a dispensing opening in said panel, said means having a lower horizontal edge portion;
a substantially horizontal mounting base extending perpendicularly from said panel rear side adjacent said lower horizontal edge portion of said opening and defining spaced parallel edges;
a fragrance cartridge selectively slidably engagable with said base, said cartridge comprising a front wall, a rear wall spaced a first predetermined distance from said front wall defining the width of said cartridge, a pair of spaced imperforate end walls joining said front and rear walls, a bottom wall, a top wall spaced a second predetermined distance from said bottom wall defining the height of said cartridge, a pair of spaced track means attached to said end walls adjacent said bottom wall for slidably engaging said edges of said base and means defining dispensing holes in a lower half of said front wall adjacent said bottom wall and in an upper half of said rear wall adjacent said top wall;
a slide selectively reciprocable between a fully closed position adjacent said base and a fully open position spaced from said base;
a front shutter defined by said slide and facially contacting both said panel rear side and said cartridge front wall, said front shutter having an imperforate surface substantially covering said dispensing opening in said panel and all of said dispensing holes in said cartridge front wall when said slide is in said fully closed position, and spaced a predetermined distance from said base less than said length of said cartridge when said slide is in said fully open position;
a rear shutter defined by said slide and spaced from said front shutter said width of said cartridge, said rear shutter facially contacting said cartridge rear wall and having an imperforate surface substantially covering all of said dispensing holes in said cartridge rear wall when said slide is in said fully closed position and spaced a predetermined distance from said base greater than said length of said cartridge when said slide is in said fully open position;
handle means extending from said front shutter through said dispensing opening for selectively reciprocating said slide;
whereby, the front shutter serves as a positive stop for positioning the cartridge on the base between the shutters; and said rear shutter provides clearance for slidably engaging the cartridge on the base when the slide is in the fully open position to facilitate replacement of the cartridge.

* * * * *